(12) United States Patent
Brisberger

(10) Patent No.: US 6,206,986 B1
(45) Date of Patent: Mar. 27, 2001

(54) METHOD AND APPARATUS FOR MONITORING AND CONTROLLING THE QUALITY OF A GALVANNEALED COATING OF STEEL STRIP

(75) Inventor: Rolf Brisberger, Issum (DE)

(73) Assignee: SMS Schloemann-Siemag Aktiengesellschaft, Dusseldorf (DE)

(*) Notice: Subject to any disclaimer, the term of this patent is extended or adjusted under 35 U.S.C. 154(b) by 0 days.

(21) Appl. No.: 09/377,353

(22) Filed: Aug. 19, 1999

(30) Foreign Application Priority Data

Aug. 24, 1998 (DE) .............................. 198 38 332

(51) Int. Cl.[7] .............................. C21D 11/00; C21D 1/48
(52) U.S. Cl. .......................... 148/508; 148/533; 266/100
(58) Field of Search .................................. 148/508, 533; 266/100, 112

(56) References Cited

U.S. PATENT DOCUMENTS 3,058,840 * 10/1962 Kerr et al. .............................. 117/93
3,307,968 * 3/1967 Schnedler .............................. 117/114
5,785,772 * 7/1998 Deka ..................................... 148/508

OTHER PUBLICATIONS

Patent Abstracts of Japan, vol. 017, No. 382 (C–1085), Jul. 19, 1993 & JP 05 065614 A (Nippon Steel Corp) Mar. 19, 1993.
Patent Abstracts of Japan, vol. 1997, No. 10, Oct. 31, 1997 & JP 09 145638 A (Kawasaki Steel Corp) Jun. 6, 1997.

* cited by examiner

Primary Examiner—Daniel J. Jenkins
Assistant Examiner—Nicole Coy
(74) Attorney, Agent, or Firm—Friedrich Kueffner

(57) ABSTRACT

A method and an apparatus for monitoring and controlling the quality of the galvannealed coating of steel strip immediately following the galvannealing step, wherein the hot galvanized coating of the steel strip produced by hot dipping is converted into FeZn phases by diffusion reactions through a thermal treatment in an annealing furnace at temperatures above the melting point of zinc. The measurement value used for the quality of the galvannealed coating of the steel strip is the visual appearance of the galvannealed coating recorded by a visual recording device in the form of measurement signals as the quality measurement value, wherein the measurement signals are processed by measurement technology and the resulting measurement values are used after conversion into control variables for the direct control of the annealing furnace.

12 Claims, 1 Drawing Sheet

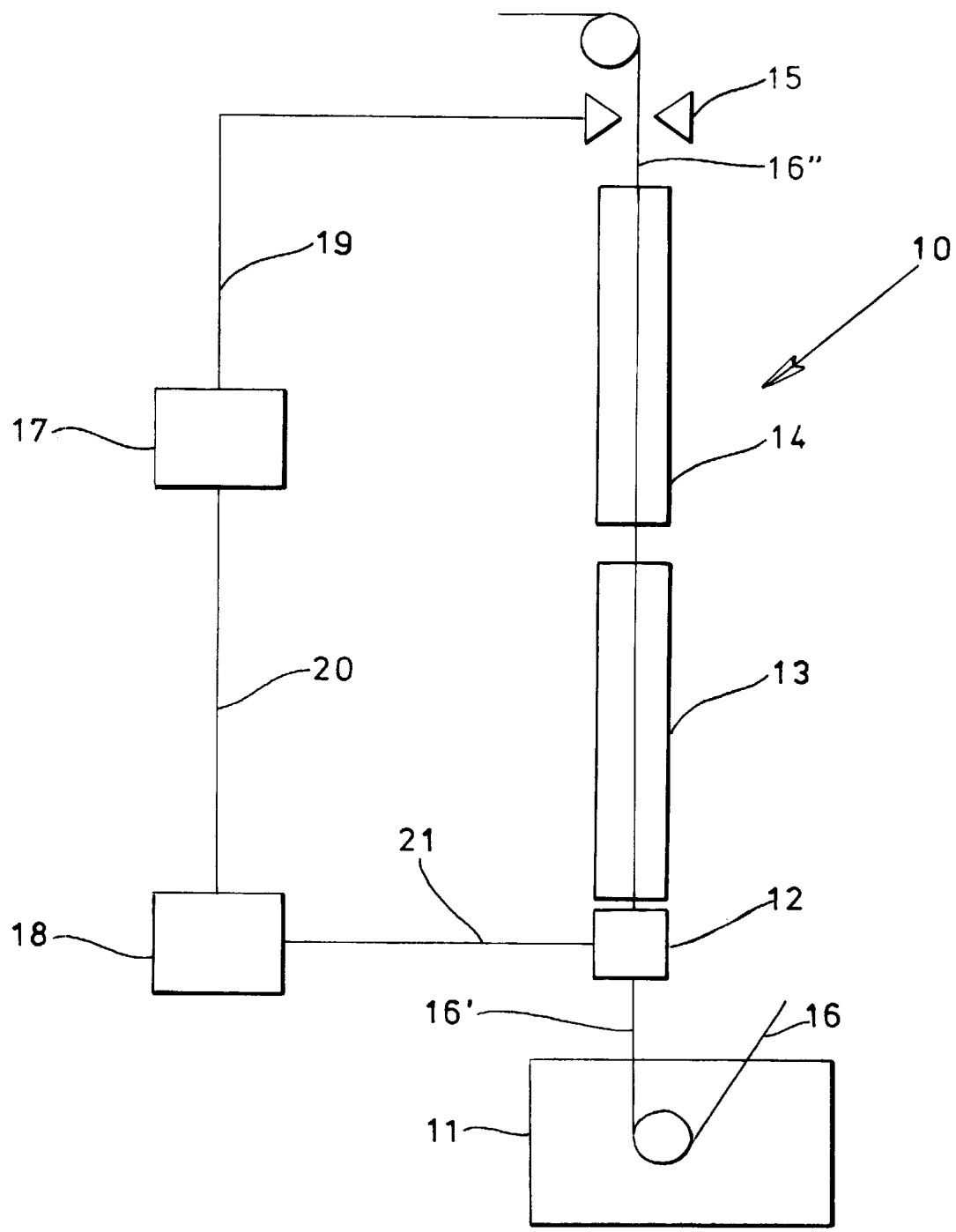

METHOD AND APPARATUS FOR MONITORING AND CONTROLLING THE QUALITY OF A GALVANNEALED COATING OF STEEL STRIP

BACKGROUND OF THE INVENTION

1. Field of the Invention

The present invention relates to a method and an apparatus for monitoring and controlling the quality of the galvannealed coating of steel strip immediately following the galvannealing step, wherein the hot galvanized coating of the steel strip produced by hot dipping is converted into FeZn phases by diffusion reactions through a thermal treatment in an annealing furnace at temperatures above the melting point of zinc.

2. Description of the Related Art

In order to improve the corrosion protection, the protection against wear, the surface hardness or the sliding behavior of metals, but also for reasons of a better appearance, it is known in the art to provide the metals with a coating with another metal, for example, to provide iron with a coating of zinc or chromium.

Various known methods have been found for applying the coating. They are:

Galvanic coatings, wherein the metal coating is applied in suitable baths containing acids or aqueous solutions by electrolysis of the metal immersed in the baths. When this method is used, coating thicknesses of up to about 10 $\mu$m are achieved;

Hot dip coatings, wherein the coatings are produced by immersing the metal to be coated in baths of liquid molten metal. In this method, a thin alloy layer is formed as a result of reactions between the metal atoms of the liquid coating metal and the atoms of the base metal, wherein a layer of pure coating metal is then placed on the alloy layer. The coating layer thicknesses achieved by this method are significantly higher than those achieved by galvanizing and are, for example, in the case of galvanizing iron (hot galvanizing) 4–50 $\mu$m; an improvement of the hot dip coatings can be achieved by Galvannealing, wherein the term galvannealing is coined by combining the words galvanizing and annealing.

In the case of galvannealing, the steel strip which emerges from the molten metal bath and is now hot galvanized is thermally aftertreated by annealing at temperatures above the melting point of zinc. During this annealing step, diffusion processes take place which also penetrate through the upper layer composed of pure coating metal, i.e., zinc, so that different FeZn phases are formed.

When the galvannealing process is carried out in an optimum manner, the coating contains about 10–12% Fe. Higher Fe contents of greater than 12% Fe lead to an unfavorable deformation behavior of the steel strip, wherein increased powdering occurs during a later deformation.

In the case of lower Fe contents of less than 9% Fe, the coating is not yet completely alloyed through and residual zinc remains at the surface of the coating. This leads to an undesirable non-uniform appearance with inhomogeneous product properties.

In order to obtain a galvannealed coating which is reacted through in an optimum manner, the thermal treatment must be controlled with respect to the duration of the treatment and with respect to the temperature level to values which are adjusted to the layer thickness. Possible control variables for the duration of the treatment are the length of the annealing zone of the annealing furnace and the speed of the steel strip, and a possible control variable for the temperature is the temperature of the annealing furnace.

At the present time, monitoring and controlling the quality of the galvannealed coating is carried out on a large technical scale in such a way that the temperature of the steel strip above the galvannealing furnace is used as the parameter for the quality of the coating. However, this type of measurement, which is carried out without contact by means of pyrometers, has the problem that a change of the emission behavior of the strip surface at the moment of complete alloying of the coating and also with continuing formation of the alloy in the galvannealed state takes place. There is also the danger that an indicated temperature difference is not the result of an actual difference, but is caused by a changed emission. Consequently, a properly functioning control based on this measured temperature cannot be carried out satisfactorily.

Another disadvantage of the temperature measurement is the fact that the ideal temperature for reaching the desired galvannealed state depends on the reaction behavior of the steel, on the bearing weight, on the aluminum content in the zinc bath and on the temperatures during galvanizing. The galvannealing temperature mentioned above constitutes only an indirect measurement and must be considered in relation to the material used and the galvanizing conditions. The statement of an optimum galvannealed temperature can only always refer to a specific material and a specific combination of the galvanizing parameters which have an influence on the galvanizing process.

Another possibility for determining the quality of the galvannealed coating by measurement technology in order to carry out a control is the combination of temperature measurement and the Fe measurement at the cold measuring location. A disadvantage is the position of the measuring location which may be up to 100 m behind the galvannealing furnace and another disadvantage is the unsatisfactory accuracy of the iron measuring device. Also, it is not possible to recognize differences in the alloying condition over the strip width.

SUMMARY OF THE INVENTION

Therefore, it is the primary object of the present invention to provide a method and an apparatus for carrying out the method which make it possible to measure the quality of the galvannealed coating by realistic measurement technology as closely as possible to the annealing furnace, so that it is possible to monitor and safely control the quality of the coating.

In accordance with the present invention, the measurement value used for the quality of the galvannealed coating of the steel strip is the visual appearance of the galvannealed coating recorded by means of a visual recording device in the form of measurement signals as the quality measurement value, wherein the measurement signals are processed by measurement technology and the resulting measurement values are used after conversion into control variables for the direct control of the annealing furnace.

Residual zinc is clearly visible to the naked eye because of its metal shine. The galvannealed coating has a light grey dull or mat appearance. With an increasing degree of alloying toward higher Fe contents, a change in color toward dark grey takes place. With the appropriate experience and from an appropriate location, the condition of the galvannealed coating can be predetermined and evaluated purely visually.

In accordance with the present invention, this visual appearance is measured as a quality measurement value and is processed by measurement technology in such a way that a direct control of the annealing furnace is possible. For this purpose, the visual appearance of the galvannealed coating is recorded by means of a suitable visual recording device and is compared to a predetermined standard. Using suitable software, the occurring differences are converted into measurement signals which can then be used for the direct continuous control of the annealing furnace.

The visual recording devices used may be, for example, light-optical devices, such as a video camera. However, other conventional recording devices can be used with the appropriate software and a suitable standard if they are capable of recording with appropriate sensitivity the special surface changes (metal shine of the residual zinc or shades of grey) which indicate the quality of the galvannealed coating.

In accordance with a feature of the present invention, recording of the visual appearance by means of a recording device can be carried out immediately following the thermal treatment, i.e., immediately behind the annealing furnace. This provides the advantage that the control of the annealing furnace can be carried out more quickly. However, it is possible to carry out the recording only after cooling which takes place after the thermal treatment because the visual appearance corresponds exactly to the final state and is no longer changed by reactions during cooling, for example, crystallization.

In order to monitor the quality of the galvannealed coating in an optimum manner, the recording of the visual appearance of the coating takes place over the entire width of the steel strip so that it is possible to monitor the entire steel strip surface during the travel of the steel strip.

Since different galvannealed coating qualities may occur at the upper and the lower surfaces of the strip during annealing or during cooling of the strip, an advantageous further development of the present invention provides that the visual appearance is recorded above and/or below the steel strip.

An apparatus for monitoring the quality of the galvannealed coating and for controlling the quality by a direct control of the annealing furnace includes at least one visual recording device which is arranged immediately following the annealing furnace or, in accordance with an alternative embodiment of the invention, behind the cooling device arranged downstream of the annealing furnace. The visual recording device is connected through measurement signal lines to a measuring and processing device in which the measurement signals of the recorded appearance are compared to a standard and any differences are then converted into measurement values by means of suitable software. Theses measurement values are introduced through measurement value lines to a control unit of the annealing furnace in which the measurement values are converted into control values for controlling, for example, the temperature of the annealing furnace or the length of the annealing section.

In order to record the entire steel strip width, a further development of the present invention provides that several visual recording devices are arranged above and/or below the steel strip and uniformly distributed over the entire width of the steel strip, or at least one visual recording device which can be swivelled is arranged below and/or above the steel strip.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

BRIEF DESCRIPTION OF THE DRAWING

The single FIGURE of the drawing is a schematic illustration of a galvannealing plant according to the present invention.

DESCRIPTION OF THE PREFERRED EMBODIMENTS

In the illustrated embodiment of the galvannealing plant 10 according to the present invention, initially the steel strip 16 is guided through a zinc bath 11 which is filled with molten zinc. As a result, a layer of FeZn alloy phases is deposited on the steel strip surface as a result of diffusion reactions, wherein the outer surface of the layer is surrounded with a layer of pure Zn. The steel strip 16' which has been changed with respect to its surface properties in this manner is now conducted into a combination of an inductively heated annealing furnace 12 and an equalizing furnace 13 which is heated electrically or by gas. The layer of FeZn phases and pure zinc applied on the steel strip 16' further reacts in these furnaces at a temperature which is above the melting point of zinc, wherein a partial quantity of the pure zinc is also converted into FeZn phases as a result of diffusion reactions.

Following the equalizing furnace 13, cooling of the steel strip 16' takes place in a cooling unit 14 from which the steel strip 16" then emerges with a completely reacted galvannealed coating. Arranged at this location immediately following the cooling units 14 are visual recording devices 15 which record the visual appearance of the galvannealed coating below and above the steel strip 16". The recorded measurement signals are transferred through a measurement signal line 19 to a measurement and processing unit 17 in which the signals are converted by means of a standard and a suitable software into measurement values which are introduced through another line, the so-called measurement value line 20, into a control unit 18 for the inductively heated annealing furnace 12 and are converted in the unit 18 into control values. The control values required for an optimum direct and continuous control of the furnace 12 are then introduced into the furnace 12 from the control unit 18 through the control line 21.

In the illustrated embodiment, in which the thermal treatment by annealing is carried out in a combination of two furnaces, i.e., an inductively heated annealing furnace 12 and a subsequent equalizing furnace 13, it would also be possible in accordance with the present invention to control only the equalizing furnace 13 to carry out the desired reactions in the galvannealed coating, or also to control both furnaces 12, 13 if this should be required. In addition, using suitable software, it would also be possible to record visual appearance at different locations, for example, directly following annealing and additionally after cooling, in order to record in this manner the progress of the desired reactions and to achieve an even more optimum quality of the galvannealed coating.

While specific embodiments of the invention have been shown and described in detail to illustrate the inventive principles, it will be understood that the invention may be embodied otherwise without departing from such principles.

I claim:

1. A method of monitoring and controlling a quality of a galvannealed coating of a steel strip immediately following a galvannealing step, the method comprising converting the hot galvanized coating produced by hot dipping through a thermal treatment in an annealing furnace at temperatures above the melting point of zinc into FeZn phases by diffusion reactions, the method further comprising using as a measurement value for the quality of the galvannealed coating of the steel strip a visual appearance of the galvannealed coating using a visual recording device and processing the measurement signals into measurement values, and, after converting the measurement values into control values, using the measurement values for a direct control of the annealing furnace.

2. The method according to claim 1, comprising carrying out monitoring and controlling continuously, comparing the measurement signals to a predetermined standard using suitable software, and using any differences as measurement values for the continuous control of the annealing furnace.

3. The method according to claim 1, comprising carrying out monitoring of the quality at least one of above and below the steel strip over an entire strip width.

4. The method according to claim 1, comprising recording the visual appearance of the galvannealed coating of the steel strip as the quality measurement value immediately following the thermal treatment.

5. The method according to claim 1, comprising recording the visual appearance of the galvannealed coating as the quality measurement value immediately following a cooling step which takes place after annealing.

6. An apparatus for monitoring and controlling a quality of a galvannealed coating of a steel strip immediately following galvannealing in an annealing furnace with a cooling unit arranged following the annealing furnace, the apparatus comprising at least one visual recording device for visually continuously recording a surface of the galvannealed coating of the steel strip, further comprising a control unit for the annealing furnace and a measuring and processing unit connecting the recording device and the control unit.

7. The apparatus according to claim 6, wherein the visual recording device is arranged immediately following the annealing furnace.

8. The apparatus according to claim 6, wherein the visual recording device is arranged following the cooling unit.

9. The apparatus according to claim 6, comprising a plurality of visual recording devices arranged uniformly distributed at least one of above and below the steel strip.

10. The apparatus according to claim 6, wherein at least one visual recording device capable of being swivelled is arranged above or below the steel strip.

11. The apparatus according to claim 6, wherein the visual recording device is a light-optical recording device.

12. The apparatus according to claim 11, wherein the visual recording device is a video camera.

* * * * *